(12) United States Patent
Beck et al.

(10) Patent No.: US 11,679,923 B2
(45) Date of Patent: Jun. 20, 2023

(54) PACKAGING FOR ORAL CARE TOOL

(71) Applicant: Sage Products, LLC, Cary, IL (US)

(72) Inventors: David P. Beck, Crystal Lake, IL (US); Brett C. Blabas, Naperville, IL (US); Ronald C. Cagle, Crystal Lake, IL (US); Thomas Keaty, Jr., Crystal Lake, IL (US); Heather K. Mercier, Geneva, IL (US); Jay R. Roberts, Barrington, IL (US)

(73) Assignee: Sage Products, LLC, Cary, IL (US)

( * ) Notice: Subject to any disclaimer, the term of this patent is extended or adjusted under 35 U.S.C. 154(b) by 0 days.

(21) Appl. No.: 17/541,462

(22) Filed: Dec. 3, 2021

(65) Prior Publication Data
US 2022/0177211 A1 Jun. 9, 2022

Related U.S. Application Data

(60) Provisional application No. 63/121,627, filed on Dec. 4, 2020, provisional application No. 63/165,984, filed on Mar. 25, 2021.

(51) Int. Cl.
*B65D 75/36* (2006.01)
*A61B 50/30* (2016.01)
*A61B 50/00* (2016.01)

(52) U.S. Cl.
CPC ............ *B65D 75/366* (2013.01); *A61B 50/30* (2016.02); *B65D 75/367* (2013.01); *A61B 2050/0065* (2016.02); *B65D 2203/02* (2013.01)

(58) Field of Classification Search
CPC ................ B65D 75/366; B65D 75/367; B65D 2203/02; A61B 50/30; A61B 2050/0065
(Continued)

(56) References Cited

U.S. PATENT DOCUMENTS 4,324,331 A * 4/1982 Ignasiak .................... A61L 2/26
206/370
5,379,895 A * 1/1995 Foslien .................. A61B 50/30
206/363
(Continued)

FOREIGN PATENT DOCUMENTS

DE 29618648.9 U1 12/1996
JP 2000-159266 A 6/2000
(Continued)

OTHER PUBLICATIONS

International Search Report and Written Opinion for International Application No. PCT/US2021/042012, dated Oct. 28, 2021, 17 pages.
(Continued)

*Primary Examiner* — Jacob K Ackun
(74) *Attorney, Agent, or Firm* — Foley & Lardner LLP

(57) ABSTRACT

A package for enclosing an oral care device includes a first layer and a second layer removably coupled to the first layer. The second layer includes a first section configured to enclose a first portion of an oral care device, a second section configured to enclose a second portion of the oral care device, and a formed region disposed between the first section and the second section, wherein the formed region is configured to prevent the first portion from moving from the first section into the second section.

9 Claims, 3 Drawing Sheets

(58) Field of Classification Search
USPC .................................. 206/467, 470, 471
See application file for complete search history.

(56) References Cited

U.S. PATENT DOCUMENTS

| | | | | | |
|---|---|---|---|---|---|
| 5,386,908 | A | * | 2/1995 | Sinn | ................. A61B 17/06133 206/363 |
| 5,392,909 | A | * | 2/1995 | Hackett | .............. A61B 50/3001 206/451 |
| 5,396,678 | A | | 3/1995 | Bredall et al. | |
| 5,765,254 | A | | 6/1998 | O'Halloran | |
| 6,059,106 | A | * | 5/2000 | Baker | .................... B65D 75/22 206/467 |
| 6,108,849 | A | | 8/2000 | Weihrauch | |
| 6,131,737 | A | * | 10/2000 | Marshall | .............. B65D 75/368 206/525 |
| 6,889,829 | B2 | * | 5/2005 | Lev | ......................... A61C 17/22 206/362.2 |
| 6,945,397 | B2 | * | 9/2005 | Brattesani | .............. B65D 75/54 206/362.2 |
| 7,784,429 | B2 | * | 8/2010 | Chiodo | .................... A61D 3/00 119/755 |
| 8,181,786 | B1 | | 5/2012 | Alas | |
| 8,245,844 | B2 | * | 8/2012 | Sorrentino | ......... B65D 21/0202 206/362.1 |
| 2005/0087464 | A1 | | 4/2005 | Brattesani et al. | |
| 2006/0021166 | A1 | | 2/2006 | Hills | |
| 2009/0197220 | A1 | | 8/2009 | Cindrich | |
| 2012/0170967 | A1 | | 7/2012 | Faison | |
| 2012/0241347 | A1 | * | 9/2012 | Bowers | ................ B65D 75/323 53/433 |
| 2016/0198990 | A1 | | 7/2016 | Betancur et al. | |

FOREIGN PATENT DOCUMENTS

| | | |
|---|---|---|
| WO | WO-2012/087317 | 6/2012 |
| WO | WO-2013/090659 | 6/2013 |
| WO | WO-2016/059035 | 4/2016 |
| WO | WO-2020/118235 | 6/2020 |

OTHER PUBLICATIONS

International Search Report and Written Opinion for International Application No. PCT/US2021/061716, dated Mar. 7, 2022, 16 pages.

\* cited by examiner

PACKAGING FOR ORAL CARE TOOL

CROSS-REFERENCE TO RELATED APPLICATIONS

This application claims the benefit of and priority to U.S. Provisional Application No. 63/165,984, filed Mar. 25, 2021, and U.S. Provisional Application No. 63/121,627, filed Dec. 4, 2020, all of which are hereby incorporated by reference in their entireties.

BACKGROUND

The present invention relates generally to the field of packaging and, more specifically, packaging for an oral care device.

Oral care tools are used in clinical settings for a variety of different uses. To facilitate the various uses, the oral care tools may require one or more modular components, accessories, or cleaning solutions to facilitate use.

Accordingly, it would be advantageous to provide packaging for an oral care tool that enables ease of access to the oral care tool and allows for all-in-one packaging, wherein the oral care tool can be packaged with one or more components, accessories, and/or cleaning solutions.

SUMMARY OF THE INVENTION

A package for enclosing an oral care device includes a first layer and a second layer removably coupled to the first layer. The second layer includes a first section configured to enclose a first portion of an oral care device, a second section configured to enclose a second portion of the oral care device, and a formed region disposed between the first section and the second section, where the formed region is configured to prevent the first portion from moving from the first section into the second section.

In various embodiments, the package includes a third section configured to enclose a third portion of the oral care device and a fourth section configured to enclose a fourth portion of the oral care device. In some embodiments, the third section includes a plurality of axially stacked folds. In other embodiments, the fourth portion is frustoconical in shape. In yet other embodiments, the formed region includes a first stepped portion and a second stepped portion, where each of the first and the second stepped portions have a width smaller than at least one of the first section or the second section. In various embodiments, the formed region is tapered such that a width of the formed region adjacent the first section is greater than a width of the formed region adjacent the second section. In some embodiments, the package further includes a collapsible region disposed between the first section and the second section, where the collapsible region is configured to facilitate movement of the first portion within the package. In other embodiments, the package includes a region disposed adjacent an uppermost portion of the package, wherein the first layer and the second layer are separated. In some embodiments, at least one of the first section or the second section is generally cylindrical in shape and has a substantially semi-circular cross-section. In other embodiments, at least one of the first section or the second section has a constant width. In yet other embodiments, the second section is thermoformed.

Another aspect of the present disclosure relates to a package system for enclosing an oral care device. The system includes a first package including a first layer and a second layer removably coupled to the first layer. The second layer includes a first section configured to enclose a first portion of an oral care device, a second section configured to enclose a second portion of the oral care device, and a formed region disposed between the first section and the second section, where the formed region is configured to prevent the first portion from moving from the first section into the second section. The system also includes a secondary package including at least one of a component of the oral care device or an accessory configured for use with the oral care device.

In various embodiments, the system also includes at least one label region, where the at least one label region includes one or more indicia. In some embodiments, the one or more indicia includes at least one of a visual indicator or a tactile indicator. In other embodiments, the first package corresponds to a first oral care treatment step and the second package corresponds to a second oral care treatment step. In yet other embodiments, the first package is configured to enclose a handle of the oral care device and the second package is configured to enclose a first attachment of the oral care device. In various embodiments, the second package is configured to enclose a plurality of oral care solution receptacles. In some embodiments, each of the plurality of oral care solution receptacles contains at least one of a cleaning solution, a cleaning paste, or a medication. In other embodiments, the formed region is configured to conform to at least one of a shape or size of the oral care device. In yet other embodiments, the formed region is configured to receive a ridge of the oral care device.

This summary is illustrative only and should not be regarded as limiting.

BRIEF DESCRIPTION OF THE DRAWINGS

The disclosure will become more fully understood from the following detailed description, taken in conjunction with the accompanying figures, wherein like reference numerals refer to like elements, in which.

The foregoing and other features of the present disclosure will become apparent from the following description and appended claims, taken in conjunction with the accompanying drawings. Understanding that these drawings depict only several embodiments in accordance with the disclosure and are therefore, not to be considered limiting of its scope, the disclosure will be described with additional specificity and detail through use of the accompanying drawings.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

According to one aspect of the present disclosure, a package for enclosing an oral care device includes a first layer and a second layer removably coupled to the first layer. The second layer includes a first section configured to enclose a first portion of an oral care device, a second section configured to enclose a second portion of the oral care device, a third section configured to enclose a third portion of an oral care device, a fourth section configured to enclose a fourth portion of an oral care device, and a formed region disposed between the second section and the third section, wherein the formed region is configured to prevent the second portion from moving from the second section into the third section.

In other embodiments, the package includes a collapsible region disposed between the third section and the fourth section, wherein the collapsible region is configured to facilitate movement of the first portion within the package.

Another aspect of the present disclosure relates to a package system for enclosing an oral care device. The package system includes a first package, and a secondary package including at least one of a component of the oral care device or an accessory configured for use with the oral care device. The first package includes a first layer and a second layer removably coupled to the first layer. The second layer includes a first section configured to enclose a first portion of an oral care device, a second section configured to enclose a second portion of the oral care device, a third section configured to enclose a third portion of an oral care device, a fourth section configured to enclose a fourth portion of an oral care device and a formed region disposed between the second section and the third section, wherein the formed region is configured to prevent the section portion from moving from the second section into the third section.

In various embodiments, the package system further includes at least one label region, the at least one label region comprising one or more indicia.

Figure 1:
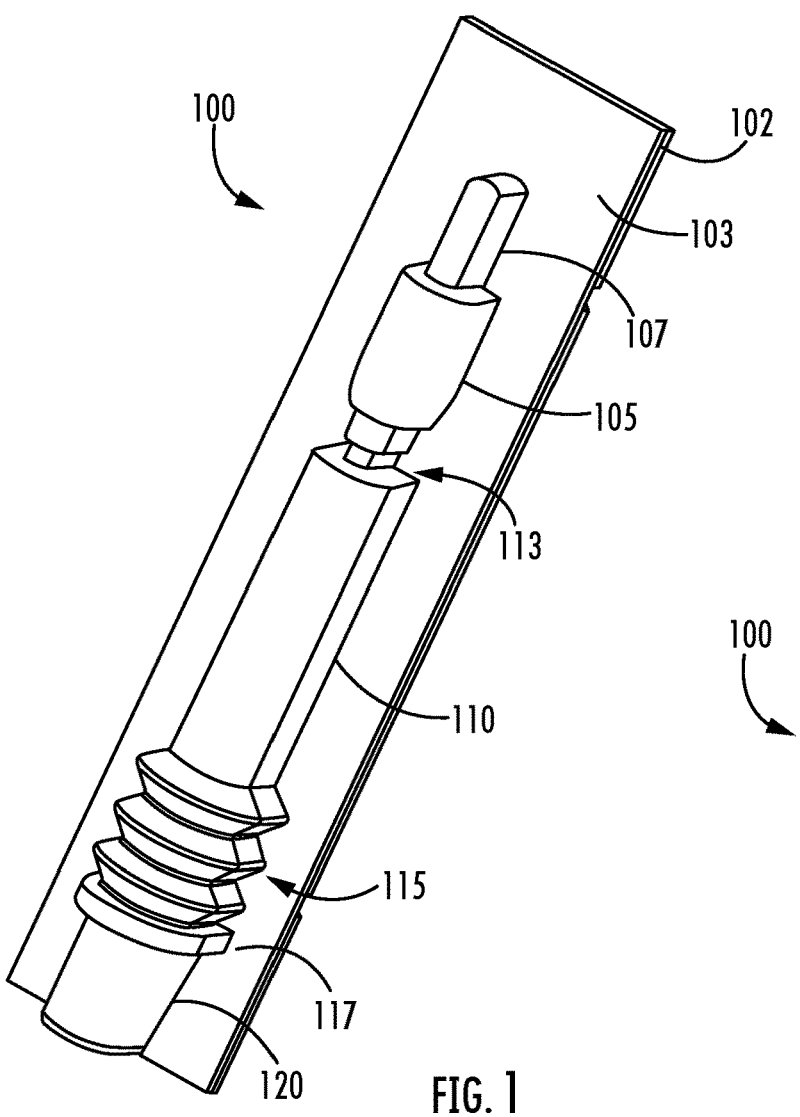
FIG. 1 is a perspective view of a package for an oral care device, according to an exemplary embodiment.
Figure 2:
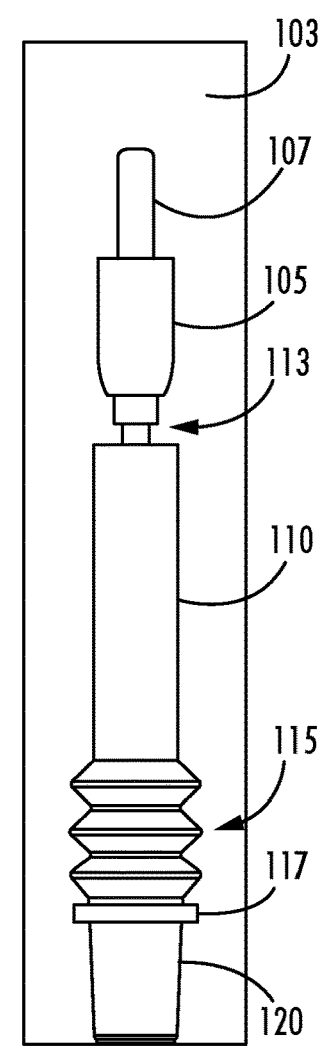
FIG. 2 is a front view of the package of FIG. 1

Referring to FIGS. 1 and 2, perspective and front views of a package 100 for an oral care device are shown, according to an exemplary embodiment. The package 100 may be configured to enclose the oral care device, one or more portions of the oral care device, one or more components couplable to the oral care device, one or more accessories for use with the oral care device, and/or more cleaning solutions intended for use with the oral care device ("device"). The package 100 includes a first layer 102 and a second layer 103, wherein the second layer 103 is coupled to the first layer 102 to enclose an oral care device therebetween. In various embodiments, the first layer 102 may be a paper, plastic, or foil backing, configured to be separable from the second layer 103. In various embodiments, the first and second layers 102, 103 may be coupled via one or more fasteners, adhesives, or a combination thereof. In various embodiments, the first and second layers 102, 103 may be recouplable or resealable. In various embodiments, the first and second layers 102, 103 are recouplable or resealable along respective outer perimeters of each of the first and second layers 102, 103. The second layer 103 may be a thermoformed plastic or polymeric layer configured to accommodate enclosing the oral care device therein. In various embodiments, the first and second layers 102, 103 may include one or more materials suitable for thermal and/or chemical sterilization including, but not limited to, autoclaving. As shown in FIGS. 1 and 2, the package 100 includes a first section 107, a second section 105, a third section 110, and a fourth section 120. In various embodiments, the first section 107 may be configured to enclose a lumen of the oral care device or a coupling region of a component for the oral care device. The first section 107 may have a generally cylindrical shape, having a substantially semi-circular cross-section. In other embodiments, the first section 107 may be rectangular. In yet other embodiments, the first section 107 may have a variable width to conform to a particular shape and/or size of the device lumen. The second section 105 may be configured to enclose a handle of the oral care device. In some embodiments, the second section 105 may have a generally cylindrical shape, having a substantially semi-circular cross-section. In other embodiments, the second section 105 may have a variable width (e.g., the second section 105 may taper from the first section 107 to the third section 110) to accommodate a shape or size of the device handle. The third section 110 may be configured to enclose a lumen and/or a functional end (e.g., brush head) of the oral care device. The third section 110 may have a generally cylindrical shape, having a substantially semi-circular cross-section. In some embodiments, a width of the third section 110 may be constant throughout. In other embodiments, the width of the third section 110 may vary to accommodate a shape or size of the device lumen and/or functional end. The fourth section 120 may be configured to enclose one or more accessories and/or a functional fluid (e.g., cleaning solution) for use with the oral care device. In some embodiments, the fourth section 120 may be rounded to have a generally cylindrical shape. In other embodiments, the fourth section 120 may have a generally frusto-conical shape. The fourth section 120 may have a greater width adjacent formed region 117. In yet other embodiments, the fourth section 120 may be rectangular. The fourth section 120 may also be formed to have any shape suitable to complement a shape or size of the one or more accessories and/or the functional fluid used with the oral care device.

Between each of the sections 107, 105, 110, 120, the package 100 may include one or more formed portions, wherein each of the formed portions conforms to one or more contours of the device (e.g., oral care device, oral care device portion, oral care device component, or oral care device accessory) enclosed within the package 100. In some embodiments, the package 100 may be formed by placing at least one oral care device and/or one or more components or accessories thereof on the first layer 102, placing the second layer 103 thereon, and coupling (e.g., pressing, thermoforming) the second layer 103 onto the first layer 102 such that the second layer 103 conforms to the one or more contours of the device (and/or its components or accessories). As shown, the oral care package 100 includes a formed region 113 disposed between the second section 105 and the third section 110. The package 100 also includes a formed region 117 disposed adjacent the fourth section 120. Each of the formed regions 113, 117 prevents movement of the device (e.g., oral care device, oral care device portion, oral care device component, or oral care device accessory) from one of the sections 107, 105, 110 into an adjacent section of the package 100. In various embodiments, the formed region 117 may include a circumferentially formed recess having a diameter or width larger than at least one of the third section 110, a region 115 disposed between the third section 110 and the fourth section 120, or the fourth section 120. For example, the formed region 113 prevents movement of the device or device portion from within the second section 105 into the third section and the formed region 117 prevents movement of the device (or device portion or device accessory) from within the fourth section 120 into the region 115 or the third section 110. In various embodiments, the device or components thereof may include one or more ridges (e.g., circumferentially disposed ridges), which may be received within at least one of the formed region 113 or the formed region 117 to prevent axial movement the device within the package 100. As shown, region 115 is configured to be a collapsible region configured to collapse in size responsive to an axial force. The region 115 may include axially stacked folds such that the region 115 has a generally accordion shape, where the region 115 may decrease in axial length (i.e., collapse) in response to an axial force (i.e., a force applied in a direction generally aligned with a primary axis of the package 100). In various embodiments, the collapsible region 115 may be configured to enable a functional end (e.g., brush head) of an oral care device enclosed within the third section 110 to be moved within the package such that is disposed adjacent to the fourth section 120. In some embodiments, the region 115 may have a constant outer width (i.e., a width of an outermost portion of a fold) and a constant inner width (i.e., a width of an innermost portion of a fold) throughout the region 115. In other embodiments, at least one of an outer width or an inner width of the region 115 may vary. In some embodiments, at least one of a length (i.e., a length defined between the end of the third section 110 and the start of the fourth section 120), the inner width, or the outer width of the region 115 may be based on at least one of a size or shape of the functional end of the oral care device. For example, the inner width of the region 115 may correspond to an outer diameter or width of the functional end of the oral care device.

Figure 3:
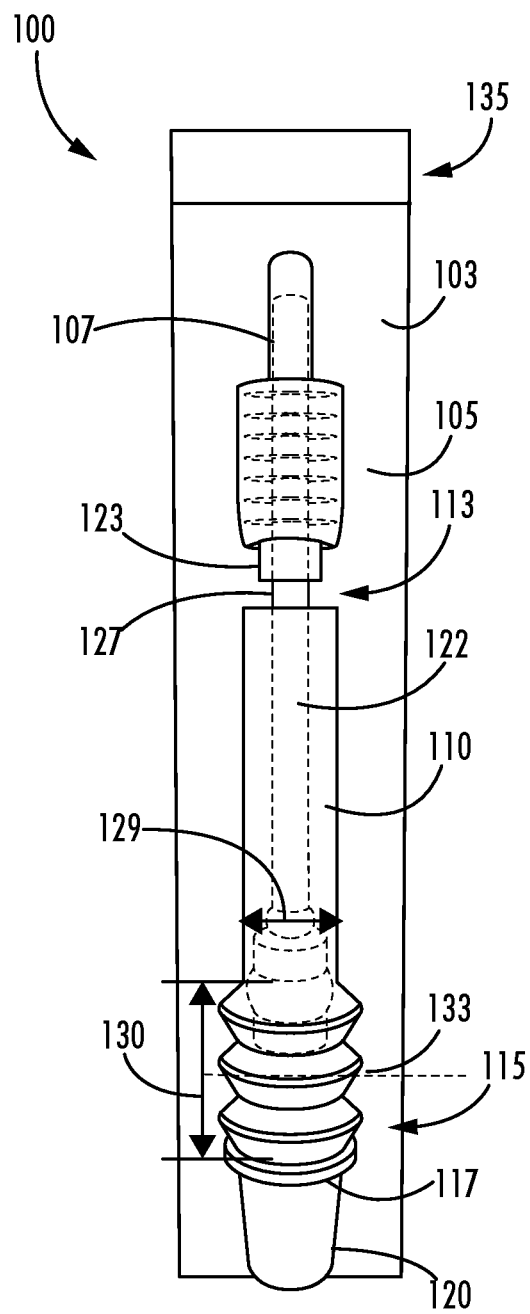
FIG. 3 is a front view of the package of FIG. 1 with an oral care device positioned therein in a first position, according to an exemplary embodiment.

FIG. 3 shows a front view of the package 100 enclosing an oral care device 122, according to an exemplary embodiment. As shown, the package 100 is configured such that a first end or lumen of the oral care device 122 is enclosed within the first section 107, a handle of the oral care device 122 is enclosed within the second section 105, a lumen and brush head of the oral care device 122 are enclosed within the third section 110, and a cleaning solution receptacle for use with the oral care device 122 is enclosed within the fourth section 120. As shown, the formed region 113 includes a first stepped portion 123 and a second stepped portion 127, wherein each of the first and second stepped portions 123, 127 have a diameter or width smaller than a diameter or width of either the second section 105 or the third section 110. Accordingly, the stepped portions 123, 127 prevent downward movement of the handle of the oral care device 122 from within the second section 105 into the third section 110 or movement of the lumen and brush head of the oral care device from within the third section 110 into the second section 105. In various embodiments, the region 113 may have a generally cylindrical shape with a substantially semi-circular cross-section. In other embodiments, the width of the region 113 may vary to accommodate a shape or size of the device lumen and/or functional end. In yet other embodiments, the width of the region 113 may decrease between an upper portion of the region 113 adjacent the second section 105 and a lower portion of the region 113 adjacent the third section 110 such that the region 113 tapers. In various embodiments, at least one of a width of the stepped portion 123 and a width of the stepped portion 127 may correspond to a width of the lumen of the device, or correspond to a protruding feature (e.g., ridge, handle, etc.) disposed on an outer surface of the lumen of the device.

Prior to use of the oral care device 122, the brush head of the oral care device 122 may be saturated with cleaning solution from within the cleaning solution receptacle enclosed within the fourth section 120. Accordingly, prior to use of the oral care device 122, the brush head of the oral care device 122 may be moved through the package 100 (i.e., pushed in a downward direction) to submerge the brush head within the solution contained in the receptacle enclosed within the fourth section 120. To facilitate movement of the brush head of the oral care device 122 through the package 100, the collapsible region 115 may collapse such that a height 130, defined between upper and lower portions of the collapsible region 115, decreases such that the brush head of the oral care device 122 is disposed adjacent to or disposed within the fourth section 120.

In various embodiments, the cleaning solution receptacle enclosed within the fourth section 120 includes an upper ridge, which is configured to be received or enclosed within the formed region 117 to prevent the receptacle from moving through the package 100 toward the third section 110. In various embodiments, the package 100 may be configured to contain a brush head or functional end of the oral care device 122 within the third section 110. In other embodiments, the package 100 may be configured to contain the brush head or functional end of the oral care device 122 within a portion of the collapsible region 115 at a height 133, such that the brush head or functional end of the oral care device is disposed a distance from the formed region 117 until the collapsible region 115 is collapsed upon or prior to use of the oral care device 122.

Figure 4:
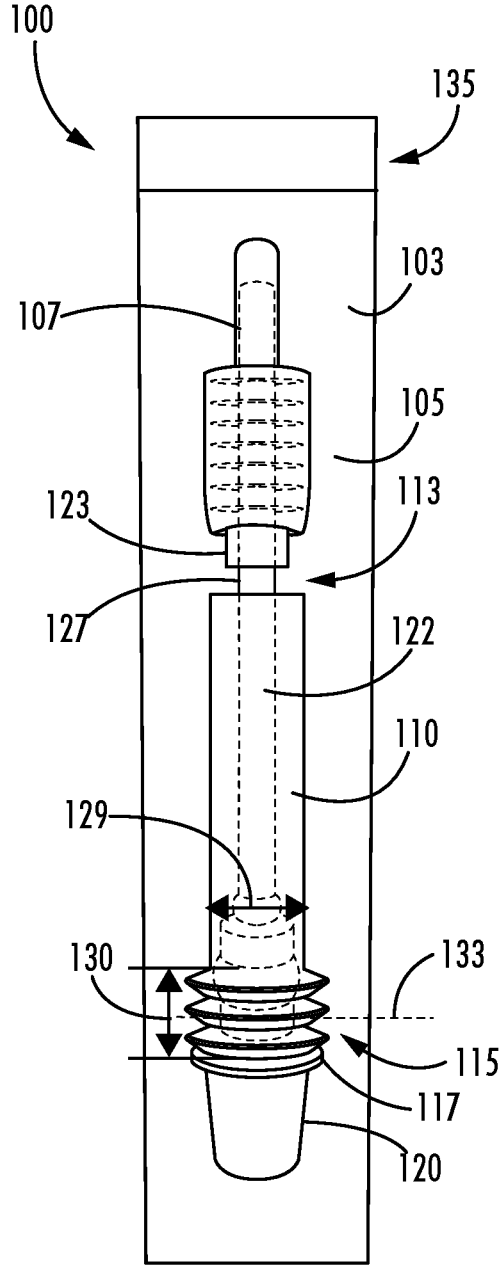
FIG. 4 is a front view of the package of FIG. 1 with an oral care device positioned therein in a second position, according to an exemplary embodiment.

FIG. 4 shows a front view of the package 100 enclosing the oral care device 122 therein, according to another exemplary embodiment. In various embodiments, a width or diameter 120 of the third section 110 may be configure to accommodate or to conform to a width or diameter of a lumen or portion of the oral care device enclosed within the third section 110. In some embodiments, the formed region 113 may be configured to taper between the second section 105 and the third section 110. As shown in FIG. 4, the formed region 113 may include a tapered edge 137 such that the formed region 113 is frustoconical in shape.

The package 100 may also include a region 135, wherein the first and second layers 102, 103 may be separated to enable access to the oral care device 122 contained therein. For example, the region 135 may be uncoupled such that a portion of the first layer 102 and a corresponding portion of the second layer 103 form tabs, which may be pulled (i.e., by a user) to separate the first and second layers 102, 103. In various embodiments, the region 135 is disposed near an uppermost portion of the package 100. In some embodiments, the region 135 may be disposed at or near a corner (i.e., defined at a junction between two perpendicular edges of the package 100). In yet other embodiments, the region 135 may be disposed along a side (i.e., parallel to a longitudinal axis of the package 100) of the package 100.

Figure 5:
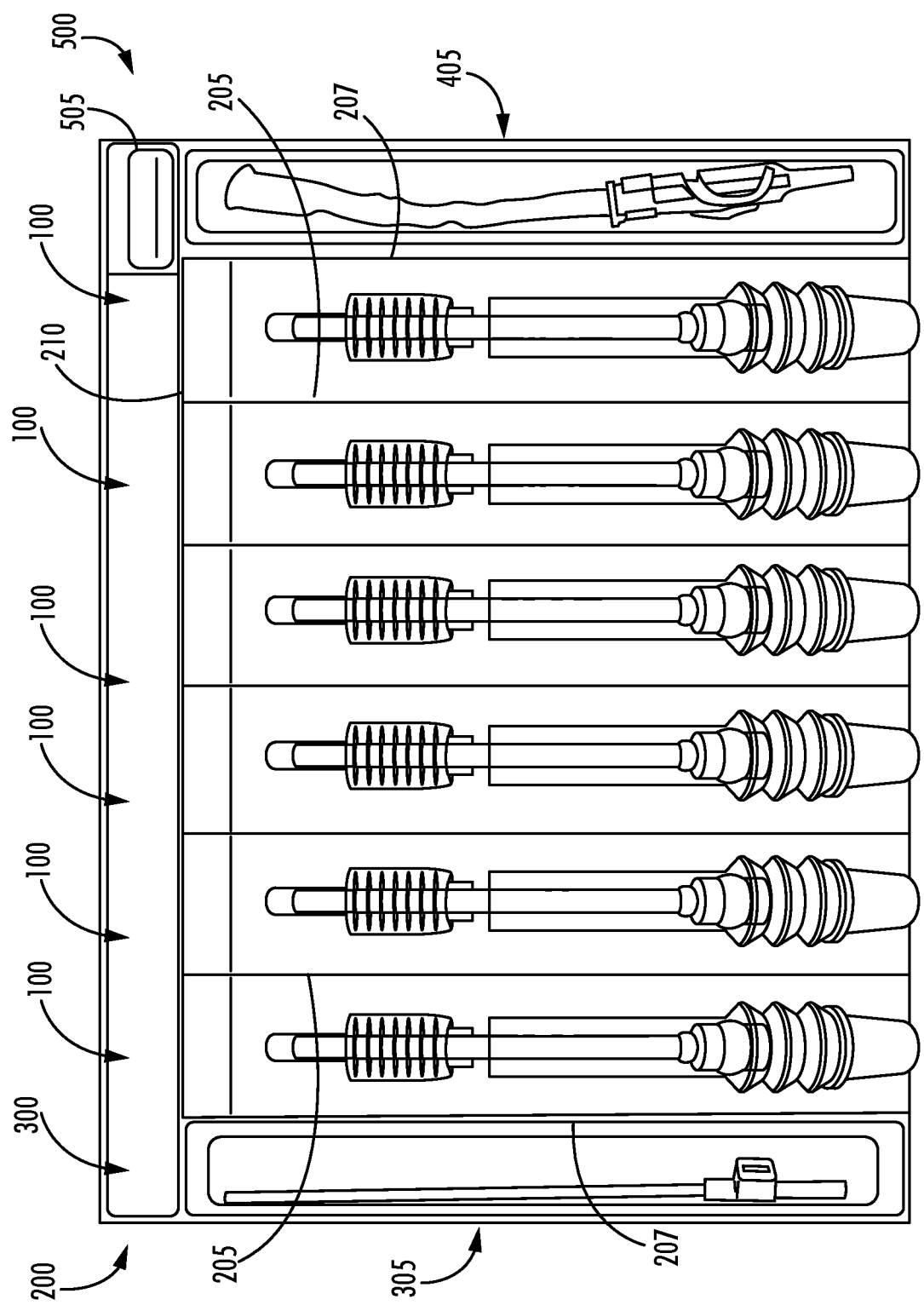
FIG. 5 is a front view of a package system for an oral care device, according to an exemplary embodiment.

In various embodiments, the package 100 may be included within a package system 200, as shown in FIG. 5. As shown in FIG. 5, a plurality of packages 100 may be mutually conjoined along perforated edges 205. Each of the packages 100 may be joined to a connector 300 along a perforated edge 210, where the connector 300 may be disposed along an upper portion along each of the packages 100. In various embodiments, the connector 300 may be configured to facilitate at least of one handling, manufacturing, or handling of the package system 200. In various embodiments, the connector 300 may include one or more layers (i.e., similar or equivalent to the layers 102, 103) or the connector 300 may include a singular layer (e.g., similar or equivalent to one of the layers 102, 103). Each of the plurality of packages 100 may enclose a device (e.g., oral care device, oral care device portion, oral care device component, or oral care device accessory). In various embodiments, the package system 200 may also include one or more accessories or components (e.g., accessories or components of or associated with an oral care device) enclosed within secondary packages 305 and 405. In various embodiments, the secondary package 305 may include a lumen with a thumb port for an oral care device enclosed within the package system 200. In various embodiments, the secondary package 405 may include a lumen with a suction control mechanism for an oral care device. The packages 100 may be removably coupled to the secondary packages 305 and/or 405 along perforated edges 207. As shown in FIG. 5, the package system 200 may also include one or more label portions 500, coupled to one or more of the packages 100 and/or secondary packages 305, 405. In various embodiments, the one or more label portions 500 include one or more regions 505, which include various indicia specifying at least one of a serial number, a date, a list of contents, or a combination thereof. In various embodiments, the one or more regions 505 may include visual (e.g., alphanumeric indicia, color coding, symbols, etc.) and/or tactile indicators (e.g., braille, ridges, bumps, embossed symbol, etc.).

In various embodiments, at least one of the packages 100 and/or the secondary packages 305, 405 may be configured to enclose a plurality of receptacles configured for use with an oral care device, wherein each of the plurality of receptacles holds at least one of a cleaning solution, a cleaning paste, or a medication. In various embodiments, each of the packages 100 within the package system 200 is configured to enclose a different component configured for use with an oral care device. For example, a first of the packages 100 may be configured to enclose a handle and lumen of the oral care device, a second of the packages 100 may be configured to enclose a lumen and a brush head of the oral care device, and a third of the packages 100 may be configured to enclose a lumen and another brush head of the oral care device. In other embodiments, a first of the packages 100 may be configured to enclose a handle of an oral care device, a second of the packages 100 may be configured to enclose a first attachment for the oral care device, and a third of the packages 100 may be configured to enclose a plurality of solution receptacles configured for use with the oral care device.

In various embodiments, an oral care device may be configured to have various components associated with corresponding various treatment steps. Accordingly, in various embodiments, the package system 200 may be configured such that each of the packages 100 and/or secondary packages 305, 405 is configured to enclose a component or tool corresponding with each of the various treatment steps. For example, a first package 100 within the package system 200 may be used for a first oral care step, a second package 100 within the package system 200 may be used for a second oral care step, and a third package 100 within the package system 200 may be used for a third oral care step. Each of the oral care steps may be based on at least one of a patient condition, a medical treatment, a time of day, a patient diet, or any other clinically relevant parameter. In various embodiments, at least one of the packages 100 and/or secondary packages 305, 405 may be configured to include a plurality of solution receptacles (e.g., plurality of cleaning solution receptacles), wherein the plurality of solution receptacles are arranged in a stack or are separated by corresponding form fitting sections within the package 100 and/or secondary package 305, 405.

Notwithstanding the embodiments described above in reference to FIGS. 1-5, various modifications and inclusions to those embodiments are contemplated and considered within the scope of the present disclosure.

As utilized herein with respect to numerical ranges, the terms "approximately," "about," "substantially," and similar terms generally mean+/−10% of the disclosed values, unless specified otherwise. As utilized herein with respect to structural features (e.g., to describe shape, size, orientation, direction, relative position, etc.), the terms "approximately," "about," "substantially," and similar terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above.

It is important to note that any element disclosed in one embodiment may be incorporated or utilized with any other embodiment disclosed herein. For example, the tapered edge 137 of the formed region 113 of the exemplary embodiment described in connection with FIG. 4 may be incorporated in the package 100 of the exemplary embodiment described in connection with at least FIG. 3. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. An oral care system comprising:
   an oral care device; and
   a package for the oral care device comprising:
   a first layer; and
   a second layer removably coupled to the first layer, wherein the second layer comprises:
   a first section configured to enclose a first portion of an oral care device;
   a second section configured to enclose a second portion of the oral care device;
   a third section configured to enclose a third portion of an oral care device;
   a fourth section configured to enclose a fourth portion of an oral care device;
   a formed region disposed between the second section and the third section, wherein the formed region is configured to prevent the second portion from moving from the second section into the third section; and
   a plurality of axially stacked folds disposed between the third section and the fourth section.

2. The oral care system of claim 1, wherein the fourth portion is frustoconical in shape.

3. The oral care system of claim 1, wherein the formed region comprises a first stepped portion and a second stepped portion, and wherein each of the first and the second stepped portions have a width smaller than at least one of the first section or the second section.

4. The oral care system of claim 1, wherein the formed region is tapered such that a width of the formed region adjacent the first section is greater than a width of the formed region adjacent the second section.

5. The oral care system of claim 1, wherein the plurality of axially stacked folds form a collapsible region disposed between the third section and the fourth section, wherein the collapsible region is configured to facilitate movement of the oral care device within the package.

6. The oral care system of claim 1, further comprising a region disposed adjacent an uppermost portion of the package, wherein the first layer and the second layer are separated.

7. The oral care system of claim 1, wherein at least one of the first section or the second section is generally cylindrical in shape and has a substantially semi-circular cross-section.

8. The oral care system of claim 7, wherein at least one of the first section or the second section has a constant width.

9. The oral care system of claim 1, wherein the second section is thermoformed.

* * * * *